United States Patent [19]

Bosley, Jr.

[11] Patent Number: 4,930,496

[45] Date of Patent: Jun. 5, 1990

[54] METHOD AND DEVICE FOR REMOVING A STONE FROM A URETER USING EXTRACORPOREAL SHOCK WAVE LITHOTRIPSY

[75] Inventor: Rodney W. Bosley, Jr., Bloomington, Ind.

[73] Assignee: Vance Products, Inc., Spencer, Ind.

[21] Appl. No.: 223,002

[22] Filed: Jul. 22, 1988

[51] Int. Cl.⁵ ............................................. A61H 1/00
[52] U.S. Cl. ................................. 128/24 A; 604/101
[58] Field of Search ................... 128/24 A, 328, 344, 128/348.1; 604/101, 22

[56] References Cited

U.S. PATENT DOCUMENTS

| | | |
|---|---|---|
| 3,827,437 | 8/1974 | Inaba . |
| 4,148,319 | 4/1979 | Kasper et al. . |
| 4,198,981 | 4/1980 | Sinnreich . |
| 4,202,346 | 5/1980 | Granier . |
| 4,243,040 | 1/1981 | Beecher . |
| 4,295,464 | 10/1981 | Shihata ............................ 128/328 |
| 4,696,668 | 9/1987 | Wilcox ........................... 604/101 X |
| 4,705,502 | 11/1987 | Patel ............................... 604/101 X |
| 4,771,777 | 9/1988 | Norzewski et al. ............ 604/101 X |

FOREIGN PATENT DOCUMENTS 1069823  11/1959  Fed. Rep. of Germany ...... 128/344

OTHER PUBLICATIONS

"Trabucco Double Balloon Ureteral Catheter ™, © Microvasive", Inc. 1988.

Cook Urological Incorporated brochure entitled "Large Balloon Dilation Catheter Set", 1988.

Primary Examiner—John D. Yasko
Attorney, Agent, or Firm—Woodard, Emhardt, Naughton, Moriarty & McNett

[57] ABSTRACT

A method of performing extracorporeal shock wave lithotripsy using a device which is a quadruple lumen catheter with one through lumen exiting at an end hole to allow the catheter to slide over a wire guide, a second lumen serving to inflate and deflate a balloon located near the distal tip of the catheter, a third lumen used to inflate and deflate a proximate balloon, a fourth lumen to supply a liquid to be delivered between the balloons and radiopaque markings for determining the position of the balloons of the catheter through X-rays of fluoroscopy. The catheter is inserted over a wire guide so that the distal balloon is located on one side of the stone in the ureter and the proximate balloon is located on the other side whereupon the balloons are inflated and the cavity formed by the balloons and the wall of the ureter is filled with fluid to surround the stone with fluid which aids in the pulverization of the stone by extracorporeal shock waves. The pulverized fragments of the stone are removed by deflating the proximate lumen and forcing water or another fluid through the fluid supply lumen. The fragments are prevented from migrating into the kidney by the distal balloon which remains inflated. The proximate balloon may be reinflated and the cavity filled with fluids and subjected to extracorporeal shock waves again to further pulverize the stone and may be deflated so that the stone fragments may be flushed down the ureter as necessary.

7 Claims, 3 Drawing Sheets

METHOD AND DEVICE FOR REMOVING A STONE FROM A URETER USING EXTRACORPOREAL SHOCK WAVE LITHOTRIPSY

BACKGROUND OF THE INVENTION

This invention relates to a method and device for removing stones from the ureter and more particularly relates to a method and device for use with extracorporeal shock wave lithotripsy.

Extracorporeal shock wave lithotripsy is used to pulverize a stone which has been isolated between the balloons of a two balloon, four lumen catheter that can be inserted over a wire guide. A fluid is injected into the isolation area to enhance the effect of an extracorporeal shock wave on the stone. Upon selective deflation of one of the balloons (while leaving the other balloon inflated), the fluid is used to wash the pulverized stone material from the isolation area prior to further subjecting the stone to extracorporeal shock waves.

It is common for stones to be formed in the renal calyces which pass into and become lodged within the ureter of an individual. Stones lodged in the ureter often cause blockage of urine produced by the kidneys, causing ureteral colic to develop which may result in severe pain to the individual. physicians prefer to avoid surgery involving incisions of the ureter in an effort to remove these stones because of the dangers and complications which might arise from such surgery. In an effort to avoid the dangers associated with major surgery, physicians have developed many different methods of treatment for ureteral stones.

Among the various methods developed to treat ureteral stones has been to prescribe spasmolytic drugs in an effort to decrease spasms in the smooth muscle of the ureteral wall which were believed to prevent passage of the stone and passage of urine around the stone. However, these spasmolytic drugs have not proven to be substantially effective in aiding a ureteral stone to be passed by the individual. Another treatment for ureteral stones is to prescribe an increase in fluid intake in hope that the increased fluid intake will cause an increased urine production which would increase the pressure above the ureteral stone thereby facilitating passage of the stone. Increased fluid intake has proven to be an ineffective means of treating ureteral stones, and in fact may result in an increase of severity of ureteral colic.

Various devices exist which are designed to extract ureteral stones without major surgery. For example, the Dormia ureteral stone dislodger uses a catheter with a retractable spring wire mechanism. The Dormia stone dislodger uses a spring wire mechanism to form a basket for entrapment of the ureteral stone. Upon entrapment of the ureteral stone, the catheter with the stone in the basket is removed through the urinary tract. This type of dislodger is effective for extraction of small ureteral stones in the lower third of the ureter.

Another type of ureteral stone extractor is a catheter with two inflatable balloons which are manipulated so that the stone is between the balloons and is then slowly withdrawn with the lower balloon acting as a dilator and the upper balloon pushing the stone toward the bladder.

Yet a further type of ureteral stone extractor with two balloons is disclosed in U.S. Pat. No. 4,295,464 to Shihata. Shihata uses an inner dislodger catheter which is slidably received within a larger outer dilator catheter. The dislodger catheter is small enough to pass beyond and arrested stone in the ureter, whereupon the balloon on the dislodger catheter may be inflated. The larger outer dilator catheter also has a balloon which ma be inflated to dilate the ureter below the stone so that the dislodger catheter may be used to apply downward force upon the stone sufficient to dislodge it from the ureteral wall. The present invention does not seek to dislodge or extract the stone from the ureter while the stone is still intact. Thus, the chances of damaging the ureter with longitudinal frictional forces applied by inflated balloons or by a stone is decreased.

The present invention relies upon extracorporeal shock waves which are directed through the body to pulverize a stone within the ureter. Typically, an extracorporeal shock wave lithotripsy patient is submerged in a bath and an ultrasonic transducer is used to transmit ultrasonic shock wave through the body directed at a stone within the ureter. The ultrasonic shock waves create forces and vibrations within the stone which cause the stone to disintegrate into small parts which may then be passed easily by the patient through the ureter and into the bladder. Many extracorporeal shock wave lithotripsy centers practice placing a ureteral catheter next to a ureteral stone. Creating some space in the ureter around the stone helps the energy from the shock waves get to the stone. The present invention improves upon extracorporeal shock wave lithotripsy by providing a two balloon multilumen catheter designed to be inserted over a wire guide which has been positioned in the ureter. The catheter is inserted over the wire guide until the balloons are upon opposite sides of the stone. The balloons are then independently inflated to localize the stone between the balloons. The catheter also has a side opening lumen with the side openings located between the balloons so that fluids can be injected through the catheter into the cavity defined by the walls of the balloon and the ureter. The fluid aids in the transmission of the ultrasonic shock waves so that they pulverize the stone more effectively. When the stone is subjected to the extracorporeal shock waves, fragments are broken off of the stone which are small enough to pass through the ureter into the bladder. At this point, the proximate balloon (that balloon located in the ureter closer to the bladder than the other balloon) is deflated and fluid is injected through the side opening lumen to wash fragments of the stone into the bladder. Upon washing the smaller fragments into the bladder, the proximate lumen may again be inflated and fluid injected into the cavity between the balloons so that the stone can again be subjected to extracorporeal shock waves. This process is repeated until the entire stone has been pulverized and washed out of the ureter whereupon the catheter is withdrawn from the patient.

The present invention does not require a tugging force on the ureter which may cause damage as is is required by various other stone extraction methods. Also, the standard extracorporeal shock wave lithotripsy is improved by providing a transmission fluid surrounding the stone to be pulverized and by localizing the area within which the shock waves need to be concentrated.

SUMMARY OF THE INVENTION

One embodiment of the present invention is a method for removing a stone from a ureter using the steps of inserting a catheter with a distal balloon, a proximate balloon and a side opening lumen with the lumen's opening positioned between the balloons into a ureter containing a stone; positioning the catheter so that the balloons are on opposite sides of the stone; inflating the balloons to form a stone containing cavity defined by the walls of the balloons and the walls of the ureter; injecting liquid through the side opening lumen into the cavity; subjecting the stone to extracorporeal shock waves to at least partially disintegrate the stone; deflating the proximate balloon; and, flushing portions of the stone from the cavity by injecting liquid through the side opening lumen.

A second embodiment of the present invention is a catheter for insertion through the ureter to surround a stone which will be removed by extracorporeal shock wave lithotripsy consisting of a catheter body containing a distal side opening inflation lumen, a proximate side opening inflation lumen, a middle side opening liquid injection lumen and an end opening through lumen. A distal occlusion type balloon is connected to the catheter body to communicate fluidly with the distal side opening inflation lumen. A proximate occlusion type balloon is connected to the catheter body to communicate fluidly with the proximate side opening inflation lumen. Independent inflation/deflation means are provided for independently inflating and deflating the distal occlusion type balloon and the proximate occlusion type balloon.

One object of the present invention is to provide a catheter which provides for localization of a stone within the ureter prior to use of extracorporeal shock wave therapy.

A second object of the present invention is to provide a catheter which contains a stone in the ureter within a defined area during subjection to shock waves and subsequent to subjection to shock wave allows the smaller portions of the pulverized stone to be washed away from the remainder of the stone.

Other objects and advantages of the present invention will be apparent from the following description.

DESCRIPTION OF THE PREFERRED EMBODIMENT

Figure 1:
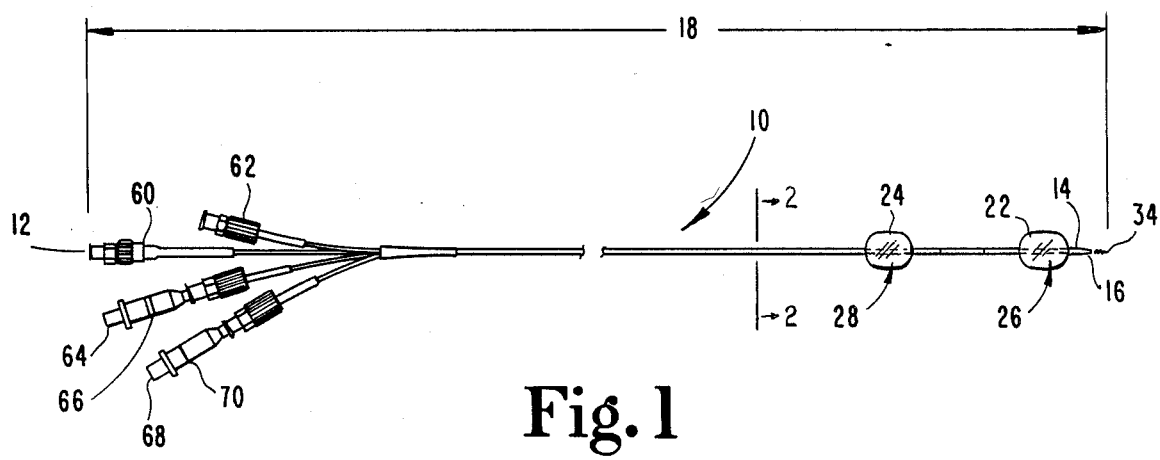
FIG. 1 is a side view of the catheter according to the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1 there is illustrated a catheter 10 having a proximate end 12 and a distal end 14. Catheter 10 has a tapered distal tip 16 to allow for the end of the catheter to be forced past a stone lodged in the ureter. The preferred embodiment of the catheter 10 has a length 18 that is 65 cm., however length 18 may be any length that is sufficient to allow the catheter to be inserted into a ureter so that the distal end 14 extends beyond a stone lodged in the ureter. The proximate end portion (that portion of the catheter to be inserted into the body) has a uniform outer diameter 20 (FIG. 2) of 6.5 French throughout a substantial portion of its length. The diameter 20 of the catheter may differ several French sizes so long as the diameter is sufficient to allow the catheter to be inserted into a ureter and past a stone lodged in the ureter. The only places where the outside diameter of the distal end portion of the catheter varies is at the locations where the two balloons, a distal balloon 22 and a proximate balloon 24, are located, and at the distal tip 16 which tapers. At the location of the distal balloon 22 and the proximate balloon 24, there are recesses 26 and 28, respectively, within which the material that forms the balloons lies when uninflated to provide balloons 22 and 24 with an uninflated outside diameter that is approximately equal to the diameter 20 of the distal end portion of the catheter 10. (See FIG. 5).

Figure 2:
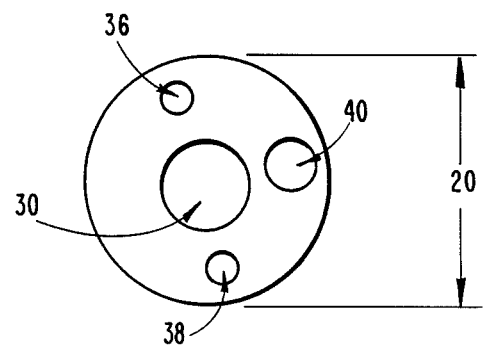
FIG. 2 is an enlarged cross sectional view of the catheter of the present invention taken in the direction of the arrows and along the line 2—2 of FIG. 1.
Figure 3:
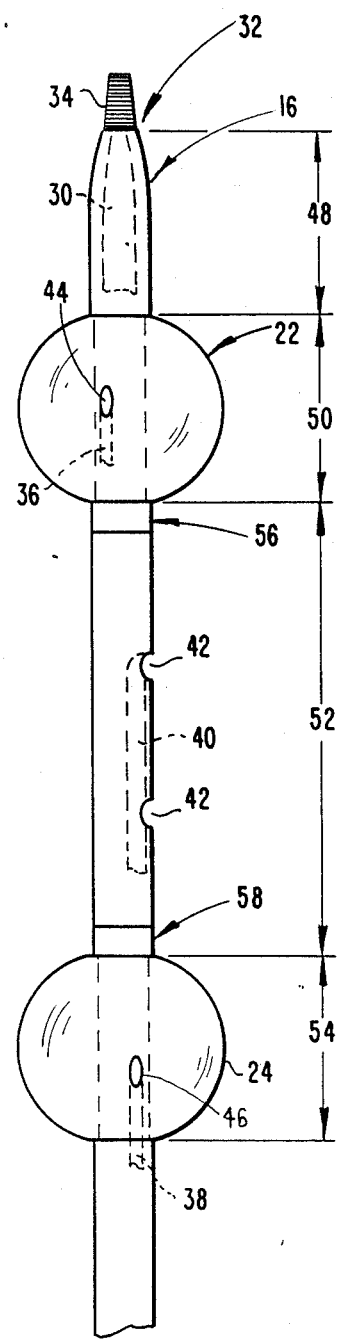
FIG. 3 is a view of the distal end portion of the catheter according to the present invention.
Figure 4:
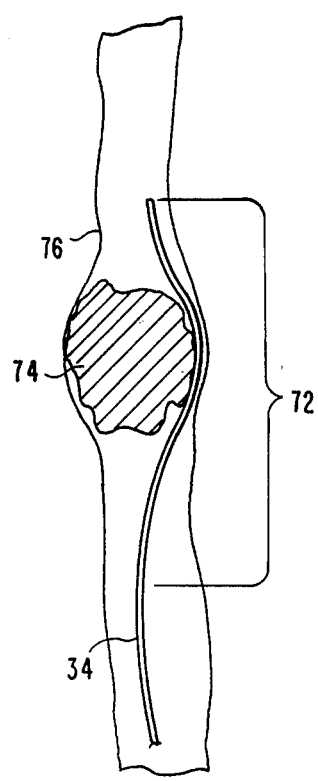
FIG. 4 is a cross sectional view of a section of a ureter with a stone lodged therein and a wire guide extending beyond the stone in the ureter.

Referring to FIGS. 1–3, catheter 10 will be more particularly described. Catheter 10 has four lumens, a through lumen 30 with an end opening 32 sized to receive a wire guide 34, a first side opening inflation lumen exiting through the side of the catheter to be in fluid communication with distal balloon, a second side opening lumen communicating with the interior of proximate balloon 24, and a side opening liquid supply lumen 40. Liquid supply lumen 40 exits through side openings 42 located between the proximate and distal balloons. Two side openings in its place are provided to insure that fluid can be injected through the lumen even when one of the openings becomes blocked. inflation lumen 36 exits through a side opening 44 located within the interior of the distal balloon 22 and inflation lumen 38 exits through a side opening 46 in the interior of the proximate balloon 24.

In the preferred embodiment, the distal balloon 22 is located a distance 48 of 1 cm from the distal end 14 of the catheter 10. The distal balloon 22 has a length 50 (and an inflated diameter) of 1 cm and is separated from the proximate balloon 24 by a distance 52 of 3 cm. Proximate balloon 24 also has a length 54 (and an inflated diameter) of 1 cm. Located on the proximate side of distal balloon 22 is a radiopaque mark 56 to locate the distal balloon 22 on the kidney side of a stone lodged in the ureter (see pictures 4–7). On the distal side of proximate balloon 24 is another radiopaque mark 58 for locating the proximate balloon on the bladder side of a stone lodged in the ureter (see FIGS. 4–7).

Each of the lumens 30, 36, 38, and 40 are independent in the sense that they do not communicate with one another within the body of the catheter. The independence of lumens 36 and 38 allows for balloons 22 and 24 to be inflated and deflated independently an selectively.

The proximate end portion of the through lumen 30 is connected in a standard manner to a female luer lock 60. This construction allows for catheter 10 to be inserted over a wire guide 34 and to have the wire guide 34 removed upon appropriate location of the catheter within the ureter and further allows for the wire guide to be reinserted prior to removing the catheter 10 for stent placement, if needed. Liquid supply lumen 40 is connected in a standard manner at the proximate end portion of the catheter 10 to a female luer lock 62 which is connectable to a fluid supply such as a saline solution or a contrast media to be delivered through lumen 40 to the area between balloons 22 and 24 through side openings 42. Inflation lumen 36 is connected in a standard manner at the proximate end portion of the catheter 10 to a female luer lock 64 which has an appropriate marking 66 to identify the balloon to which the lumen is connected. Luer lock 64 is designed to be connected to an appropriate inflation fluid which may be contained within a syringe so that the fluid may be injected into and removed from the balloon to allow for selective inflation and deflation of the balloon. Inflation lumen 38 is connected at the proximate end portion of the catheter 10 to a luer lock 68 with an appropriate marking 70 to identify the balloon to which the lumen is connected. Again, luer lock 68 is designed to be connected to a source of inflation fluid.

Through lumen 30 of the catheter accepts a 0.038 inch (0.97 mm) diameter Wire guide 34. Wire guide 34 is Teflon ® coated stainless steel wire guide that is approximately 145 cm long with a flexible tip section 72 which is approximately 3 cm long to allow for manipulation of the catheter through the ureter (see FIG. 4) and around a stone lodged therein.

Catheter 10 is manufactured of polyurethane, although it is envisioned that other biocompatible materials may be used. Balloons 22 and 24 are manufactured of latex, but could be manufactured of polyethylene terrathalad or polyethylene or PVC or other material.

Figure 5:
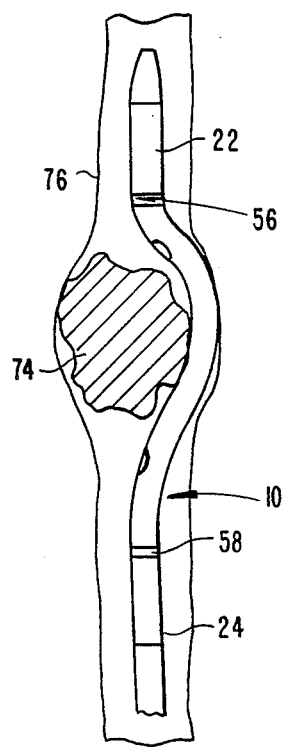
FIG. 5 is a view of the ureter of FIG. 4 with a dual balloon catheter inserted so that the uninflated balloons are on opposite sides of the stone in the ureter.

Referring to FIGS. 4–7, a method for use of a dual balloon catheter to enhance extracorporeal shock wave lithotripsy is serially illustrated. When a stone 74 has become lodged in a ureter 76, a wire guide 34 is inserted through the urinary tract into the ureter 76 with the flexible tip portion 72 of the wire guide being extended beyond the stone. The location of the flexible tip portion 72 of the wire guide 34 may be determined by X-rays or fluoroscopy. Once the tip of the wire guide 34 is located beyond the stone 74 in the ureter 76, a dual balloon catheter 10, as previously described, is inserted over the wire guide and into the ureter 76. With use of X-rays or fluoroscopy, the position of radiopaque marks 56 and 58 with respect to the stone 74 can be determined. Once radiopaque mark 56 is o the kidney side of the stone and radiopaque mark 58 is on the bladder side of stone 74, the physician is assured that distal balloon 22 and proximal balloon 24 are on opposite sides of stone 74. As illustrated in FIG. 5, during insertion of catheter 10, balloons 22 and 24 are in an uninflated state to aid in feeding the catheter 10 through the urinary tract.

Figure 6:
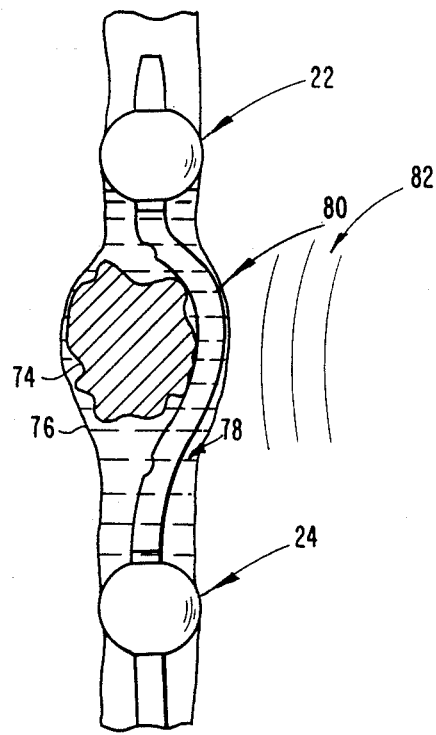
FIG. 6 is a view of the ureter of FIG. 4 with the balloons of the catheter inflated and showing a contrast medium which has been injected through a side opening lumen in the catheter into the cavity between the balloons.
Figure 7:
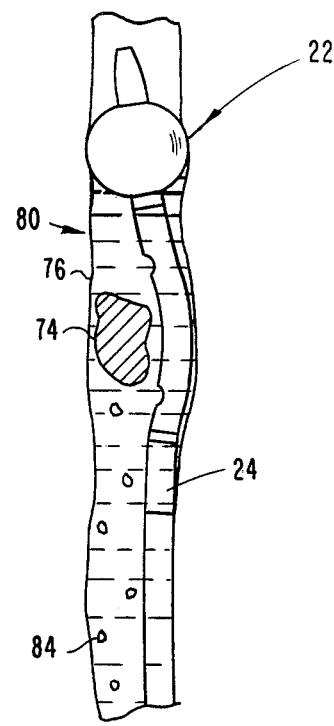
FIG. 7 is a view of the ureter of FIG. 4 after the stone has been subjected to extracorporeal shock waves and the proximate balloon of the catheter has been deflated to allow liquids exiting from the catheter side ports to expel fragments of pulverized stone down the ureter.

Once balloons 22 and 24 are located on opposite sides of stone 74 within the ureter 76, both balloons 22 and 24 are inflated as illustrated in FIG. 6. Inflation of balloons 22 and 24 causes occlusion of the ureter o both sides of the stone thereby forming a stone containing cavity 78 defined by the walls of balloons 22 and 24 and the walls of ureter 76. Upon inflation of balloons 22 and 24 with an appropriate fluid, such as saline solution or contrast media, stone containing cavity 78 is filled with and pressurized by a saline solution injected through side openings 42 of liquid supply lumen 40. It is also possible to use contrast media to fill stone containing cavity 78 to enhance disclosure of the stone during radiofluorscopy. Upon filling stone containing cavity 78 with a fluid 80, (shown as cross hatchings in FIGS. 6 and 7), the stone is subjected to ultrasonic shock waves 82. It has been discovered that ultrasonic shock waves pulverize stones more effectively when the stone is surrounded by water or another appropriate fluid because the fluid aids in transferring the energy of the ultrasonic shock wave.

After subjecting stone 74 to ultrasonic shock waves 82 for a period of time, stone 74 will be partially or completely pulverized to form stone fragments 84 which are small enough to be passed through ureter 76. To aid in irrigation of ureter 76, the proximate balloon 24 of catheter 10 is deflated while maintaining the inflation of distal balloon 2. Additional fluid 80 is then forced through liquid supply lumen 40 and out side openings 42 to flush the fragments 84 down ureter 76.

If the stone 74 is not completely pulverized by its initial subjection to extracorporeal shock waves 82, then proximate balloon 24 is inflated and the stone containing cavity 78 filled with fluid 80 as illustrated in FIG. 6 and additional extracorporeal shock waves 82 are directed at stone 74. Again, after a period of time, the proximate balloon 24 is deflated and fluid 80 is injected through liquid supply lumen 40 and out of side openings 42 to flush stone fragments 84 down ureter 76. The process of inflating the proximate balloon 24 and filling the stone containing cavity 78 with fluid 80 and subjecting the stone to extracorporeal shock waves 82 and then deflating the balloon 24 and flushing fragments 84 down ureter 76 may be repeated until stone 74 is sufficiently pulverized that the entire stone is removed from the ureter 76. Upon sufficient pulverization of the stone 74, the catheter 10 is removed from the ureter 76. After removal of the catheter from the ureter, a stent may be placed in the ureter, if necessary, in which case the wire guide should be reinserted through the catheter 10 prior to its removal from the ureter. The wire guide can then be used for placing the stent.

One reason that distal balloon 22 remains inflated during the flushing process is to prevent migration of the stone fragments upwards through the ureter and back into the kidney. In order to prevent such migration of stone fragments 84 it is necessary to provide separate inflation lumens for distal balloon 22 and proximate balloon 24 as is done in the present invention.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A method for removing a stone from a ureter comprising the steps of;
   inserting a catheter having a distal balloon, a proximate balloon and a side opening lumen with the lumen's opening positioned between the balloons into a ureter containing a stone;
   positioning the catheter so that the balloons are on opposite sides of the stone;
   inflating both balloons to form a stone containing cavity defined by the walls of the balloons and the walls of the ureter;
   injecting liquid through the side opening lumen into the cavity;
   subjecting the stone to extracorporeal shock waves to at least partially disintegrate the stone;
   deflating the proximate balloon; and,
   flushing portions of the stone from the cavity by injecting liquid through the side opening lumen.

2. The method of claim 1 and further comprising the steps of:
   reinflating the proximate balloon to reform said cavity;
   reinjecting liquid into said cavity through said side opening lumen;
   resubjecting the stone to extracorporeal shock waves.

3. The method of claim 2 and further comprising the steps of:
   deflating the proximate balloon; and,
   flushing portions of the stone from the cavity by injecting liquid through the side opening lumen.

4. The method of claim 3 wherein said deflating and flushing steps are repeated after said reinflating, reinjecting and resubjecting steps.

5. The method of claim 1 wherein said inserting step further comprises the initial step of inserting a wire guide into the ureter passed the stone to be removed and said catheter is inserted over said wire guide.

6. The method of claim 1 wherein said positioning step is carried out by providing said catheter with radiopaque position indicators and said positioning is determined by X-ray.

7. The method of claim 6 wherein said positioning step is carried out by providing each balloon with a separate radiopaque position indicator and said positioning is determined by X-ray.

* * * * *

UNITED STATES PATENT AND TRADEMARK OFFICE
CERTIFICATE OF CORRECTION

PATENT NO. : 4,930,496

DATED : June 5, 1990

INVENTOR(S) : Rodney W. Bosley, Jr.

It is certified that error appears in the above-identified patent and that said Letters Patent is hereby corrected as shown below:

ON TITLE PAGE:

In the Abstract, at line 10, following the word "X-rays", the word "of" should read "or".

In column 1, at line 27, "physicians" should read "Physicians".

In column 2, at line 5, "ma" should read "may".

In column 2, at line 18, "wave" should read "waves".

In column 3, at line 37, "wave" should read "waves".

In column 4, at line 53, "inflation" should read "Inflation".

In column 5, at line 7, "an" should read "and".

In column 5, at line 36, "Wire" should read "wire".

In column 5, at line 61, the phrase "is o the" should read "is on the".

In column 6, at line 4, the phrase "ureter o both" should read "ureter on both".

UNITED STATES PATENT AND TRADEMARK OFFICE
CERTIFICATE OF CORRECTION

PATENT NO. : 4,930,496

DATED : June 5, 1990

INVENTOR(S) : Rodney W. 1990

It is certified that error appears in the above-identified patent and that said Letters Patent is hereby corrected as shown below:

In column 6, at line 28, "balloon 2." should read "balloon 22.".

Signed and Sealed this

Tenth Day of September, 1991

Attest:

HARRY F. MANBECK, JR.

Attesting Officer

Commissioner of Patents and Trademarks